United States Patent [19]
Gulavita et al.

[11] Patent Number: 5,981,574
[45] Date of Patent: Nov. 9, 1999

[54] PHENANTHROFURAN DERIVATIVES

[75] Inventors: Nanda K. Gulavita, Shrewsbury, Mass.; Catherine Heintz, Sheffield, United Kingdom; James B. McAlpine, Bolton, Mass.; Hideaki Morishige, Ibaraki, Japan; Angela M. Stafford, Sheffield, United Kingdom

[73] Assignee: Phytera, Inc., Worcester, Mass.

[21] Appl. No.: 09/038,341

[22] Filed: Mar. 11, 1998

[51] Int. Cl.$^6$ .......................... A61K 31/34; C07D 307/77
[52] U.S. Cl. ............................................ 514/468; 549/457
[58] Field of Search .............................. 549/457; 514/468

[56] References Cited
PUBLICATIONS

Ai et al., Chinese Chem. Lett. (1994), 5(2), 125–6.
Dorsaz et al. "Uncinatone, a New Antifungal Hydroquinone Diterpenoid from Clerodendrton uncinatun Schinz", Helivetica Chimica Acta 68:1605–1610 (1985).
Wang et al., "Chemical constituents of Ajuga forrestii Diels", Yaoxue Xuebao 29(12):899–904 (1994), abstract only.
Wang et al., "Ajuforrestine A, a new phenanthro[3,2–b] furan derivative from Ajuga forrestii Diels", Chin. Chem. Lett. 5(2): 125–126 (1994), abstract only.

*Primary Examiner*—Laura L. Stockton
*Attorney, Agent, or Firm*—Clark & Elbing LLP

[57] ABSTRACT

Phenanthrofuran derivatives and methods of using them to treat angiogenic diseases.

9 Claims, No Drawings

PHENANTHROFURAN DERIVATIVES

BACKGROUND OF THE INVENTION

The invention is related to phenanthrofuran derivatives whose properties include anti-angiogenic activity.

Angiogenesis, or neovascularization, is the process of the growth of capillary blood vessels. The disturbances in the regulation of angiogenesis are associated with angiogenic diseases such as arthritis, psoriasis, diabetic retinopathy, hemangiomas, and cancer including tumor growth and metastasis. Endogenous angiogenic factors include basic fibroblast growth factor (b-FGF), vascular permeability factor/vascular endothelial growth factor, angiogenin, granulocyte-colony stimulating factor (G-CSF), heparinases, interleukin 8 (IL-8), platelet derived growth factor (PD-GF), placenta growth factor, prostaglandin E1 (PGE1), prostaglandin E2 (PGE2), hepatocyte growth factor, TGF-α, TGF-β, TNF-α, and TNF-β. Anti-angiogenic factors include angiostatin, cartilage-derived inhibitor, interferon-α (IFN-α), interferon-β (IFN-β), protamine, thrombspondin, and tissue inhibitors of metalloproteinase (TIMPs).

Ajuforrestine A was isolated from the whole plant of *Ajuga forrestii* Diels (Wang et al., *Chinese Chem. Lett.* 5:125, 1994). According to Wang et al., the whole plant is used as a traditional herbal medicine for the treatment of dysentery, laryngitis, and acute and chronic nephritis (brightism).

SUMMARY OF THE INVENTION

The invention features, in part, a compound having the following formula (I):

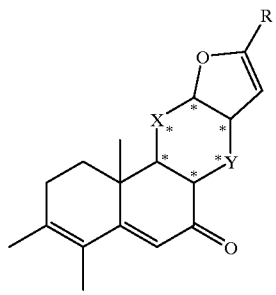

where R is methyl and each of X and Y is C—OH; or R is methyl and each of X and Y is C=O ( a quinone derivative). The six asterisks indicate $sp^2$ carbon atoms. The invention also features pharmaceutical compositions and packaged drugs containing one or more of the compounds of formula (I) or the compound ajuforrestine A (1,11b-dihydro-7,11-dihydroxy-3,4,8,11b-tetramethyl-phenanthro[3,2-b]furan-6 (2H)-one, also known as ajuforrestin A); or combinations of a compound of formula (I) and ajuforrestine; and methods of administering these pharmaceutical compositions to affect angiogenesis, for example, for treating angiogenic diseases.

DETAILED DESCRIPTION OF THE INVENTION

The invention features, in part, a novel natural product isolated from manipulated cell cultures derived from *Ajuga reptans* and pharmaceutical compositions thereof. This product has the following structure (formula I):

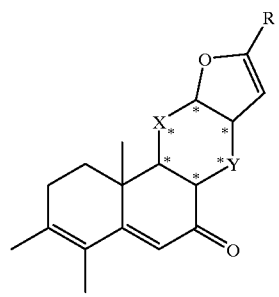

where R is methyl and each of X and Y is C—OH (formula I-A). It has been discovered that these cell cultures of *A. reptans* produce both formula (I-A) and ajuforrestine A. These compounds are useful, for example, as anti-angiogenic agents. The invention also features pharmaceutical compositions containing formula (I), or a combination of pharmaceutically active compounds including formula (I). Formula (I) includes formula (I-A), and formula (I-B) where each of X and Y is C=O and R is methyl (a quinone derivative). These compositions are useful in a method for treating angiogenic diseases. This method includes administering a pharmaceutically effective amount of a disclosed composition to a patient with one or more angiogenic diseases, such as arthritis, psoriasis, diabetic retinopathy, hemangiomas, and cancers including tumor growth or metastasis.

Formulae (I-A) and (I-B) were isolated and obtained as follows. A plant cell culture of *Ajuga reptans* (Labiatae) was prepared using young shoots of *A. reptans*. A modified medium containing 2,4-dichlorophenoxyacetic acid (2,4-D) (1 mg/L), kinetin (0.1 mg/L), 2% sucrose, and 0.5% Gelrite (Duchefa Biochemie BV, Haarlem, the Netherlands) was prepared after Murashige and Skoog (*Physiol Plant*, 15:473 1962). The surfaces of the shoots were sterilized by brief immersion in 70% ethanol followed by immersion in 15% sodium hypochlorite for 20 minutes. The sterilized shoots were chopped into small pieces approximately 5 mm long and placed upon solidified callus induction medium. Callus was established 2 months after initiation.

To establish suspension cultures, portions of established callus were placed in 20 mL liquid B39 medium, modified after Gamborg's B5 recipe (*Exp. Cell Res.*, 50:148 1968) to contain 2,4-D (5 mg/L) and 2% sucrose. The suspension media were replenished at 7–14 day intervals. After 2 months the established suspension culture was routinely maintained in a 250 mL conical flask (Erlenmeyer flask). By transferring 16 mL of 14-day old suspension culture into 100 mL fresh B39 medium. The culture was incubated at 25° C. in continuous low light, and shaken at 140 rpm.

Formulae (I-A) and (I-B) were produced by the following cell culture manipulation. A two-liter flask containing 750 mL of production medium B49 (Gamborg's B5, 5% sucrose, no hormones) was inoculated with 132 mL of 14-day old suspension culture. After 7 days of growth, filter-sterilized methyl jasmonate (250 uM final concentration) and an autoclaved *Candida albicans* preparation (50 mg/L final concentration) were added. The cell cultures were harvested by vacuum filtration after a further 4–6 days. The *C. albicans* preparation was obtained by growing a culture of ATCC 28516 on 4EPD (yeast extract 1%, yeast peptone 2%, glucose 2%) to maximum cell density and twice autoclaving the total yeast culture prior to addition to plant cultures.

After harvesting, the separated cells were freeze-dried before extraction. The remaining medium was frozen pending extraction with a solid-phase polystyrene resin such as HP-20 (Mitsubishi Chemical Industries) or XAD-4 (Rohm and Haas). The freeze-dried cells were extracted with water followed by methylene chloride/methanol (1:1). The organic extract (1.66 g) was pre-adsorbed on RP-18. A sintered funnel, 6.8 cm diameter, 5 cm height, was packed with RP-18 and the pre-adsorbed material was introduced in a 1 cm layer. The column was eluted with the following solvents under vacuum: water (200 mL), 75% water/methanol (200 mL), 50% water/methanol (200 mL), 25% water/methanol (200 mL), 100% methanol (400 mL), 50% methanol/methylene chloride (400 mL) and methylene chloride (100 mL). The 100% methanol eluate (474.1 mg) was chromatographed on a LH-20 column (52 cm×2.5 cm) with methanol to yield an active fraction (#7) of about 14 mg based on the collagen tube assay. Eleven milligrams were purified on an Ito multi-coil countercurrent apparatus on a 265 mL coil using heptane:ethyl acetate:methanol:water:5:5:5:2 with the upper phase mobile. Two compounds, formula (I-A) (5.1 mg) and ajuforrestine A (4.1 mg) were isolated.

Alternatively, formula (I-A) can be purified on a Waters Prep-Nova PACK HR C18 (3.9×300 nm) under the following conditions. The solvent is 40% water/60% acetonitrile, and the flow rate is 1 mL/minute. The compound is detected by UV at 338 nm, 290 nm, or 254 nm, and preferably at 338 nm. The minimum detection limit is 0.1 micrograms per injection. The concentration is 0.1–1 microgram per injection, preferably 1 microgram per injection.

The following analytical spectral data were obtained for formula (I-A).
UV(MeOH)$\lambda_{max}(\epsilon)$: 227(38,500), 262(17,900), 288(23,000), 333(16,700), 407(5,500); $^1$H NMR(CDCl$_3$) δ 14.12 (1H,s), 6.58(1H,s), 6.26(1H,s), 5.13(1H,s), 3.29(1H,br dd,J=5.4, 13.2 Hz), 2.53(1H,m), 2.44(3H,s), 2.22(1H,m), 1.91 (3H,s), 1.88(3H,s), 1.59(1H,m), 1.52(3H,s).
$^{13}$C NMR(CDCl$_3$) δ: 191.3, 165.9, 154.7, 151.6, 148.6, 140.9, 131.2, 129.7, 125.4, 188.6, 117.1, 109.5, 101.5, 39.5, 30.4, 29.8, 22.6, 20.7, 15.0, 14.0.
EIMS m/z: 324.1(100), 309.1(77).
HREIMS m/e: 324.1362 (C$_{20}$H$_{20}$O$_4$ requires 324.1362).

The following analytical spectral data confirming the structure of ajuforrestine A were obtained. $^1$H NMR (CDCL$_3$) δ 14.22(1H,s), 7.27(1H,s), 6.26(1H,s), 5.11(1H,s), 3.29(1H,m) 2.53(1H,m), 2.40(3H,s), 2.21(1H,m), 1.91(3H, s), 1.88(3H,s), 1.62(1H,m), 1.52(3H,s).
$^{13}$C NMR (CDCl$_3$) δ 191.4, 165.8, 154.2, 149.4, 140.9, 140.3, 131.3, 130.3, 125.4, 118.6, 118.1, 116.3, 109.3, 39.5, 30.4, 29.7, 22.5, 20.8, 15.0, 9.5.
Negative Electro-Spray MS m/z 307[M—CH$_4$—H]$^-$ Ajuforrestine A can also be obtained according to the procedures in Wang et al.

Isolation scheme for quinone formula (I-B)

Cells and medium were separated from a 38 L culture of *Ajuga reptans*. The medium was passed through a HP-20 resin. The dried resin material was eluted with CH$_3$CN and the eluate was concentrated to dryness (44.2 g). The dried eluate was partitioned with ethyl acetate/acetone/water (700 mL/125 mL/700 mL) and the ethyl acetate layer was separated. The remaining aqueous layer was further extracted with ethyl acetate (2×700 ml). The three combined organic layers were concentrated to dryness (525 mg), and fractionated on an Ito counter current chromatography instrument using the procedure above. Fractions were collected and combined according to their TLC characteristics and colors. Fourteen combined fractions were made. Combined fractions 3–5 contained ajuforrestine A, while fraction 6 (19 mg) contained formula (I-A). Fraction 10 (8.1 mg) was further purified on a small LH-20 column (26×1.5 cm) using methanol/methylene chloride to obtain pure formula (I-B) (6.8 mg). The following analytical data were obtained for the quinone (formula I-B):
$^1$H NMR (CDCl$_3$) δ 6.47(1H,q,J=0.8 Hz), 6.36(1H,s), 2.91 (1H,m), 2.55(1H,m), 2.45(3H,d,J=0.8 Hz), 2.25(1H,m), 1.88 (3H,s), 1.86(3H,s), 1.60(1H,m), 1.53(3H,s).
$^{13}$C NMR (CDCl$_3$) δ 184.1, 180.9, 175.3, 163.3, 161.0, 155.9, 150.3, 141.4, 131.4, 129.9, 125.0, 122.5, 104.8, 40.7, 31.2, 30.3, 24.6, 21.1, 15.1, 14.4.

Anti-angiogenic activity can be demonstrated by any of several methods known to those in the art, such as that described in the examples below. There are also murine dorsal air sac, rabbit eye, and chick egg models known in the art.

EXAMPLE

Example 1

Anti-angiogenic activity: collagen tube

Human umbilical-vein endothelial cells (HUVEC; Kurabo Industries, Ltd., Osaka, Japan) were cultured with M-199 medium (Gibco, Gaithersburg, Md.) with 10% PBS, bFGF (15 ng/mL; PeproTech EC, Ltd., Princeton, N.J.) and epidermal growth factor (EGF) (15 ng/mL; Upstate Biotechnology Inc., Lake Placid, N.Y.) until they become confluent. All experiments were performed using cells that were passaged at least five times. Eight volumes of type-I collagen solution (Nitta Gelatin Inc., Osaka, Japan)were mixed with one volume of 10X M-199 medium and one volume of reconstruction buffer (0.5 N NaOH, 200 mM HEPES and 260 mM NaHCO$_3$).

Collagen gel (300 μL/well) was placed in 24-well culture plates (NUNC) and incubated for 1.5 hours. HUVEC (1.4× 10$^5$/0.5 mL) were seeded in the collagen-coated plates and cultured for 2 hours at 37° C. Fifty microliters of sample were added. The collagen gel was replaced (300 μL/well), and the mixture was cultured for 1.5 hours. Three hundred fifty microliters of M-199 medium with 10% PBS, 30 ng/mL basic fibroblast growth factor (bFGF) were added, and the mixture was cultured for 20 hours. One field per well was photographed with a phase-contrast microscope, and the length of the tube structures were measured on a Macintosh computer using the public domain NIH Image program (see Table 1 for results). Erbstatin was used as a positive control for inhibition of angiogenesis. Inhibition over 100% indicates that the test compound inhibited the angiogenesis more than that observed in control cultures without bFGF.

TABLE 1

Anti-angiogenic activity in Tube Formation Assay

| Sample | 1st Assay | | | 2nd Assay | | |
|---|---|---|---|---|---|---|
| | 30 μg/ml | 10 μg/ml | 1 μg/ml | 30 μg/ml | 10 μg/ml | 1 μg/ml |
| Ajuforrestine A fraction | 102.0 | 99.6 | n.e. | 109.1 | 98.0 | n.d. |
| Formula I-A fraction | 119.3 | 119.3 | 114.8 | 107.0 | 107.8 | 107.6 |
| Erbstatin 10 μM | | 117.5 | | | 107.9 | |
| Erbstatin 1 μM | | 7.6 | | | 6.7 | | n.d.: not done, n.e.: no effect, the data represent % of inhibition

OTHER EMBODIMENTS

The essential features and advantages of the invention are apparent from the disclosure herein. Without departing from the spirit and scope of the claims, the invention can be easily adapted to other usages and conditions.

What is claimed is:

1. A compound having the following formula (I):

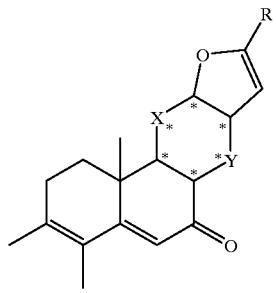

where R is methyl and each of X and Y is C—OH; or R is methyl and each of X and Y is C═O; and the six asterisks indicate sp² carbon atoms.

2. A compound of claim 1 where R is methyl and each of X and and Y is C—OH.

3. A compound of claim 1 where R is methyl and each of X and Y is C═O.

4. A pharmaceutical composition comprising a compound of the formula (I):

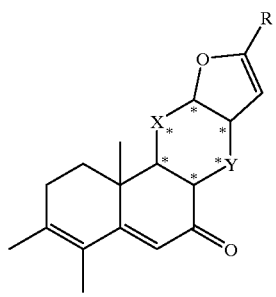

where R is methyl and each of X and Y is C—OH; or R is methyl and each of X and Y is C═O; and the six asterisks indicate sp² carbon atoms; and a pharmaceutically acceptable carrier.

5. A method for treating an angiogenic disease, said method comprising administering to a patient an anti-angiogenic effective amount of a composition comprising a compound having the formula (I):

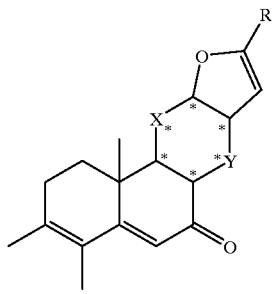

where R is methyl and each of X and Y is C—OH; or R is methyl and each of X and Y is C═O; and the six asterisks indicate sp² carbon atoms;

or said compound is ajuforrestine A;

or combinations thereof.

6. A method of claim 5, wherein said disease is selected from arthritis, psoriasis, diabetic retinopathy, and hemangioma.

7. A method of claim 6, wherein said disease is diabetic retinopathy.

8. A method of claim 5, wherein said composition comprises a compound of formula (I) where R is methyl and each of X and Y is C—OH.

9. A method of claim 5, wherein said composition comprises ajuforrestine A.

* * * * *